United States Patent
Shah et al.

(10) Patent No.: US 11,213,334 B2
(45) Date of Patent: Jan. 4, 2022

(54) BONE FRACTURE FIXATION DEVICE WITH TRANSVERSE SET SCREW AND AIMING GUIDE

(71) Applicants: Anjan Shah, Tampa, FL (US); Douglas Cerynik, Downingtown, PA (US)

(72) Inventors: Anjan Shah, Tampa, FL (US); Douglas Cerynik, Downingtown, PA (US)

(73) Assignee: Stabiliz Orthopaedics, LLC, Exton, PA (US)

( * ) Notice: Subject to any disclaimer, the term of this patent is extended or adjusted under 35 U.S.C. 154(b) by 93 days.

(21) Appl. No.: 15/288,351

(22) Filed: Oct. 7, 2016

(65) Prior Publication Data

US 2017/0100182 A1     Apr. 13, 2017

Related U.S. Application Data

(60) Provisional application No. 62/238,181, filed on Oct. 7, 2015.

(51) Int. Cl.
| | |
|---|---|
| *A61B 17/74* | (2006.01) |
| *A61B 17/88* | (2006.01) |
| *A61B 17/86* | (2006.01) |
| *A61B 17/17* | (2006.01) |

(52) U.S. Cl.
CPC ...... *A61B 17/8872* (2013.01); *A61B 17/1721* (2013.01); *A61B 17/1725* (2013.01); *A61B 17/742* (2013.01); *A61B 17/8888* (2013.01)

(58) Field of Classification Search
CPC ... A61B 17/8872; A61B 17/742; A61B 17/86; A61B 17/8861; A61B 17/746; A61B 17/8605; A61B 17/863; A61B 17/8057; A61B 2017/00004; A61B 2017/90

USPC .. 606/96, 88, 103, 87, 80, 81, 98, 179, 101, 606/102, 99, 205, 211, 62–67
See application file for complete search history.

(56) References Cited

U.S. PATENT DOCUMENTS

| | | | |
|---|---|---|---|
| 3,489,143 A | 1/1970 | Halloran | |
| 4,622,959 A | 11/1986 | Marcus | |
| 4,911,153 A * | 3/1990 | Border | A61B 17/1721 |
| | | | 606/64 |
| 5,180,383 A | 1/1993 | Haydon | |
| 5,190,544 A | 3/1993 | Chapman | |
| 5,578,035 A | 11/1996 | Lin | |
| 6,039,739 A | 3/2000 | Simon | |
| 6,126,661 A | 10/2000 | Faccioli | |
| 6,221,074 B1 | 4/2001 | Cole | |
| 6,379,360 B1 | 3/2002 | Ackeret | |
| 6,402,753 B1 | 6/2002 | Cole | |
| 6,562,042 B2 * | 5/2003 | Nelson | A61B 17/1721 |
| | | | 606/328 |
| 6,835,197 B2 | 12/2004 | Roth | |
| 7,001,388 B2 | 2/2006 | Orbay | |

(Continued)

FOREIGN PATENT DOCUMENTS

WO   WO 2010/107403   * 9/2010   ......... A61B 17/742

*Primary Examiner* — Pedro Philogene
(74) *Attorney, Agent, or Firm* — Schott, P.C.

(57) ABSTRACT

A bone fixation device for treatment of a bone fracture includes a fixation screw defining a transverse opening, a fixation arm configured for inserting the fixation screw through a bone fracture, a set screw, and an aiming arm configured for inserting the set screw into the transverse opening and engagement with the fixation screw. The set screw stabilizes the fixation screw.

20 Claims, 16 Drawing Sheets

(56) References Cited

U.S. PATENT DOCUMENTS

| | | | |
|---|---|---|---|
| 7,018,380 B2 | 3/2006 | Cole | |
| 7,569,055 B2 | 8/2009 | Zander | |
| 7,927,333 B2* | 4/2011 | Gradl | A61B 17/746 606/280 |
| 8,506,608 B2* | 8/2013 | Cerynik | A61B 17/86 606/300 |
| 9,314,283 B2* | 4/2016 | Overes | A61B 17/74 |
| 2007/0270848 A1* | 11/2007 | Lin | A61B 17/746 606/65 |
| 2010/0023011 A1* | 1/2010 | Nakamura | A61B 17/746 606/64 |
| 2010/0179550 A1 | 7/2010 | Schreiber | |
| 2014/0052132 A1* | 2/2014 | Matityahu | A61B 17/1725 606/62 |
| 2015/0134014 A1* | 5/2015 | Palmer | A61B 17/863 606/304 |
| 2017/0202566 A1* | 7/2017 | Luo | A61B 17/1725 |

* cited by examiner

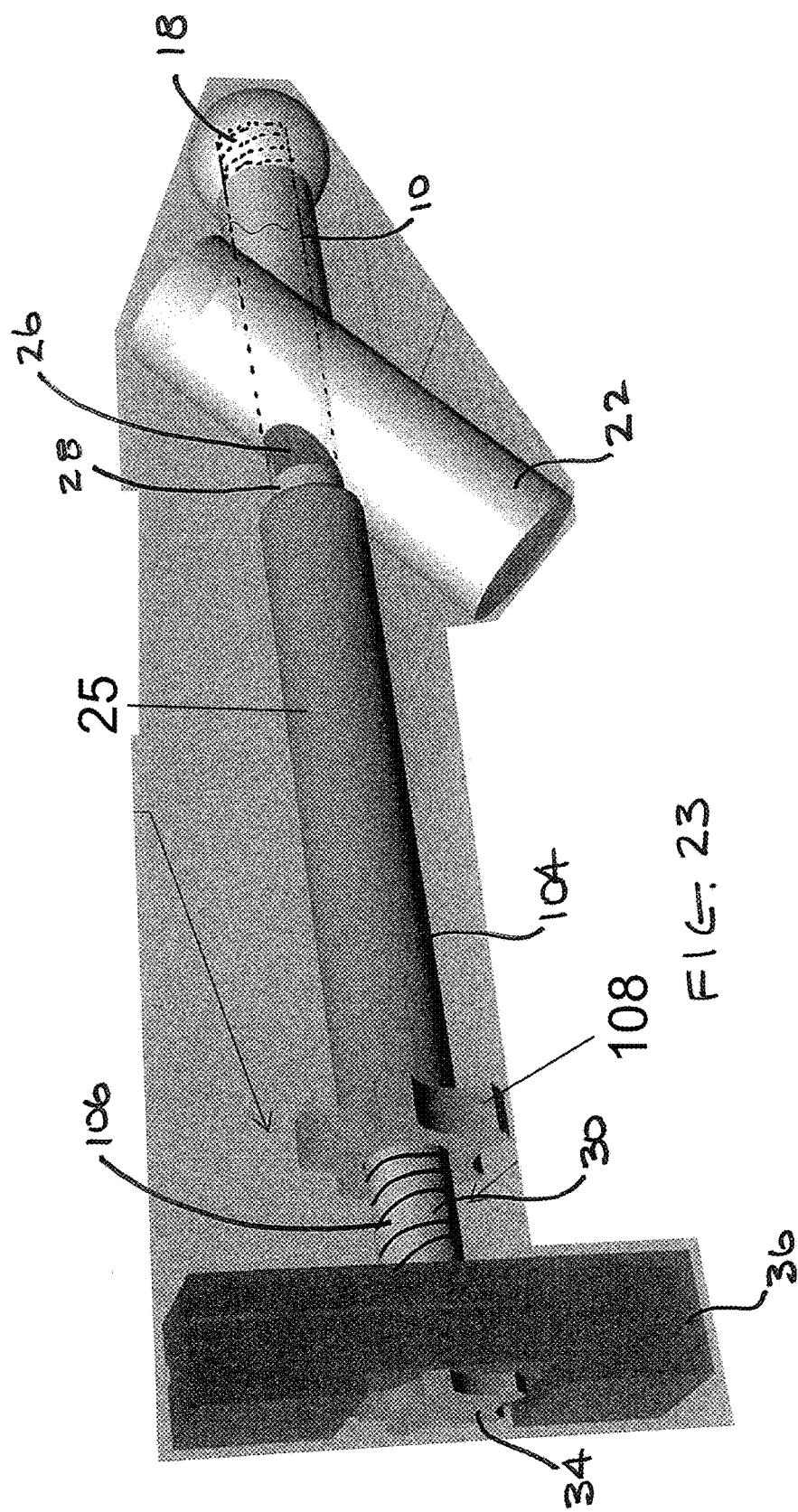

BONE FRACTURE FIXATION DEVICE WITH TRANSVERSE SET SCREW AND AIMING GUIDE

CROSS REFERENCE TO RELATED APPLICATION

This application claims the benefit of U.S. Provisional Patent Application No. 62/238,181, filed Oct. 7, 2015, which is incorporated by reference as if fully set forth.

FIELD OF INVENTION

This invention concerns fixation devices for the treatment of bone fractures. More specifically, the invention concerns devices for insertion of mechanical fixation devices for treatment of bone fractures.

BACKGROUND

FIG. 1, shows an example of a known treatment for non-displaced bone fractures of the femoral neck 10. As shown, a fracture 15 extends between through the femoral neck 10 and is fixed using multiple compression screws 12 inserted through the neck 10 of the femur 22 just below the greater trochanter 14. The threaded ends 16 of the screws 12 bite into the femur's head 18, and when the screw heads 20 of the screws 12 contact the femur 22, the femoral head 18 is drawn into contact with the femoral neck 10 to promote healing of the fracture 15.

Each individual screw head 20 has a relatively small contact area, and thus cannot distribute the compression load widely onto the bone. Furthermore, a single screw cannot provide significant resistance to rotation between the femoral head 18 and the femur 22 across the fracture 15. To compensate for this, multiple screws 12 are used to secure the fracture 15, as shown in FIG. 1A. The use of multiple screws 12 increases trauma and complicates the insertion procedure.

A need exists for a mechanism that enables fixing the fracture portions without relying on contact between the screw heads 20 and the femur 22, thereby reducing the number of screws 12 and in turn the degree of trauma to bone and tissue.

SUMMARY

The invention relates to a bone fixation device for treatment of a bone fracture, including a first fastener defining a transverse opening, a fixation arm configured for inserting the first fastener through a bone fracture, a second fastener, and an aiming arm configured for inserting the second fastener into the transverse opening and engagement with the first fastener. The second fastener stabilizes the first fastener.

The invention further relates to a bone fixation device for treatment of a femoral neck fracture, located between the femur and femur head regions. The device includes a fixation screw defining a transverse opening, and a fixation arm configured for inserting the fixation screw through the femur at a first angle. The fixation arm has an elongate body including a first end and a second end, and the fixation screw is releasably affixed at the second end of the body. The device further includes a set screw, and an aiming arm configured for inserting the set screw through the femur at a second angle into the transverse opening and engagement with the fixation screw. The aiming arm is affixed to the first end of the fixation arm and extends over the fixation arm to position the set screw in alignment with the transverse opening. The set screw stabilizes the fixation screw.

The invention further relates to a method of fixing a bone fracture, including providing a bone fixation device. The device includes a fixation screw defining a transverse opening, and a fixation arm configured for inserting the fixation screw through the femur at a first angle. The fixation arm has an elongate body including a first end and a second end, and the fixation screw is releasably affixed at the second end of the body. The device further includes a set screw, and an aiming arm configured for inserting the set screw through the femur at a second angle substantially perpendicular to the first angle, into the transverse opening and engagement with the fixation screw. The aiming arm is affixed to the first end of the fixation arm and extending over the fixation arm to position the set screw in alignment with the transverse opening. The method further includes drilling a first opening through the bone fracture to create a passage to a pilot hole, the first opening extending in a first longitudinal direction, using the fixation arm to insert the fixation screw into the pilot hole, drilling a second opening extending in a second direction that intersects the first direction, and using the aiming arm to insert the set screw into the transverse opening, to stabilize the fixation screw.

BRIEF DESCRIPTION OF THE DRAWINGS

FIG. 23 is a side isometric view of another embodiment of a device for treatment of a femoral neck fracture.

DETAILED DESCRIPTION OF THE PREFERRED EMBODIMENTS

Figure 1:
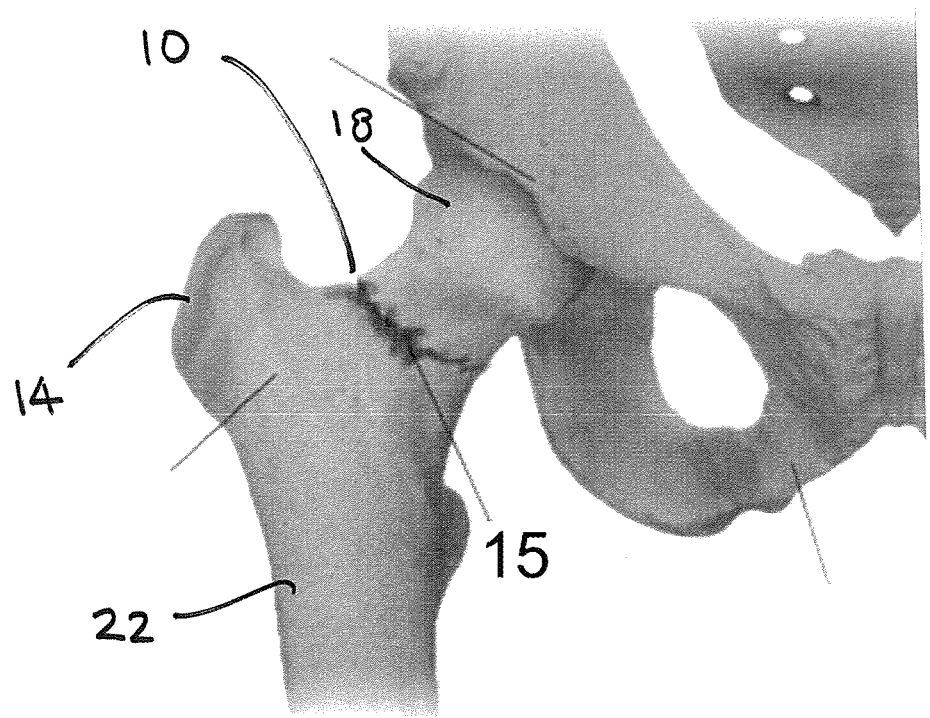
FIG. 1 is an anterior view of a femoral neck fracture and a prior art method of treatment.
Figure 1A:
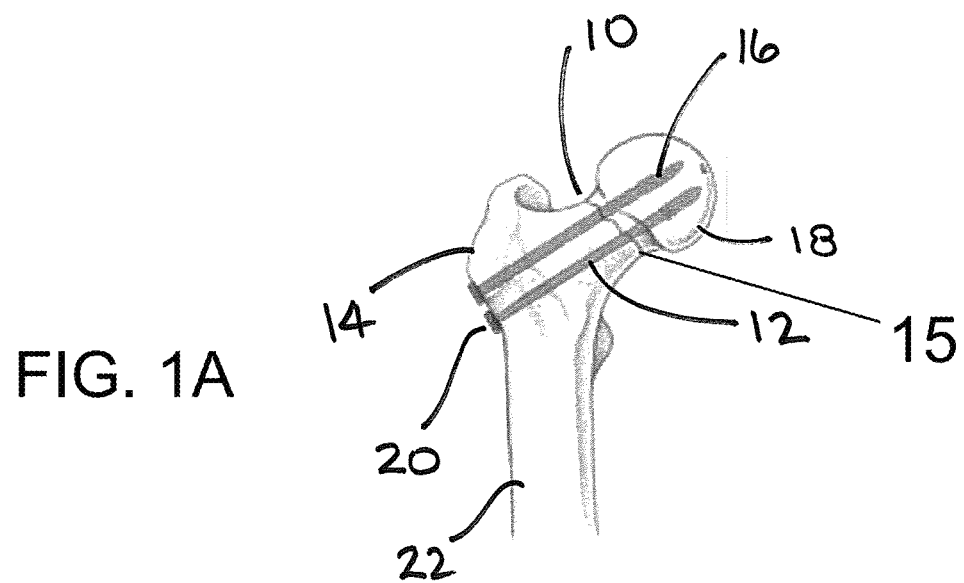
FIG. 1A is an enlarged detail of FIG. 1.

Certain terminology is used in the foregoing description for convenience and is not intended to be limiting. Words such as "front," "back," "top," and "bottom" designate directions in the drawings to which reference is made. This terminology includes the words specifically noted above, derivatives thereof, and words of similar import. Additionally, the words "a" and "one" are defined as including one or more of the referenced item unless specifically noted. The phrase "at least one of" followed by a list of two or more items, such as "A, B or C," means any individual one of A, B or C, as well as any combination thereof.

Figure 2:
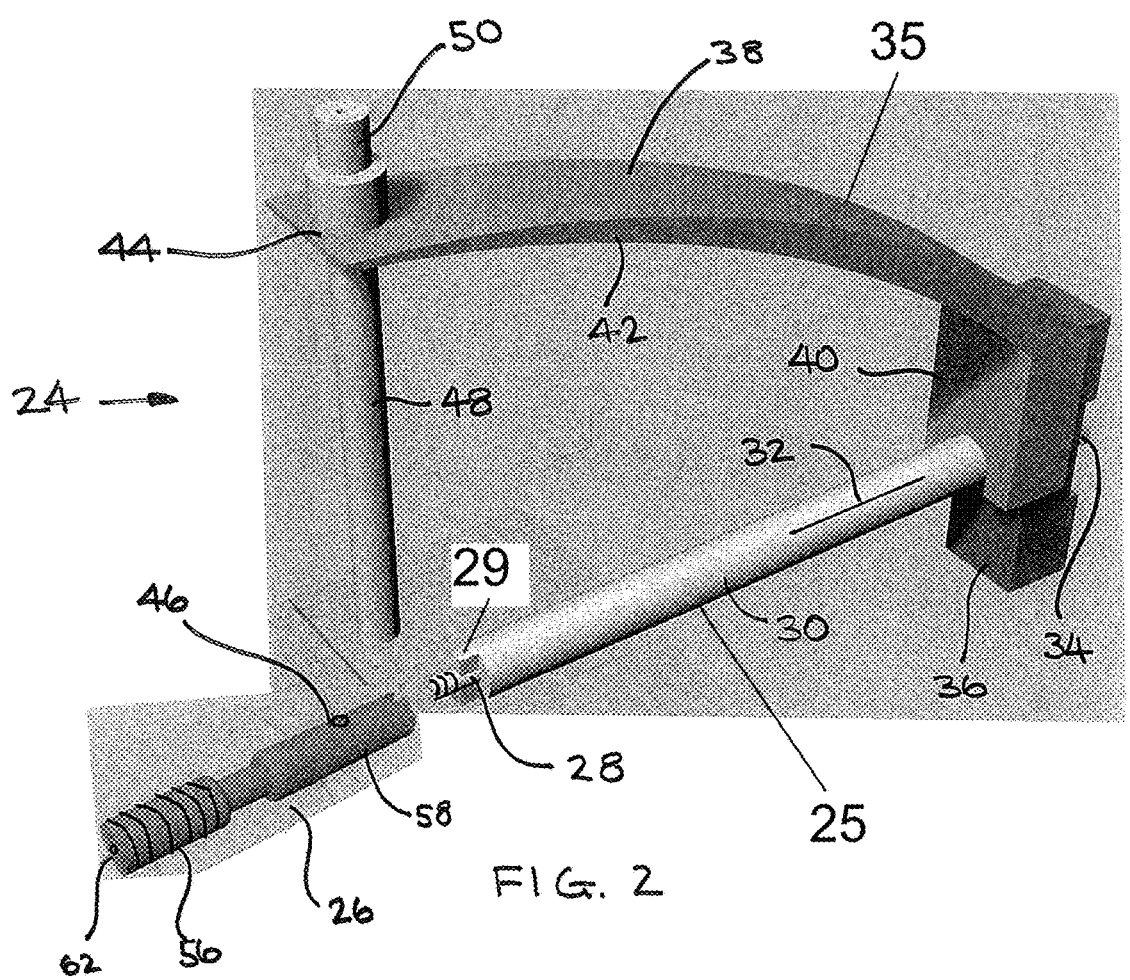
FIG. 2 is an isometric view of an exemplary device for treating bone fractures according to the invention.
Figure 3:
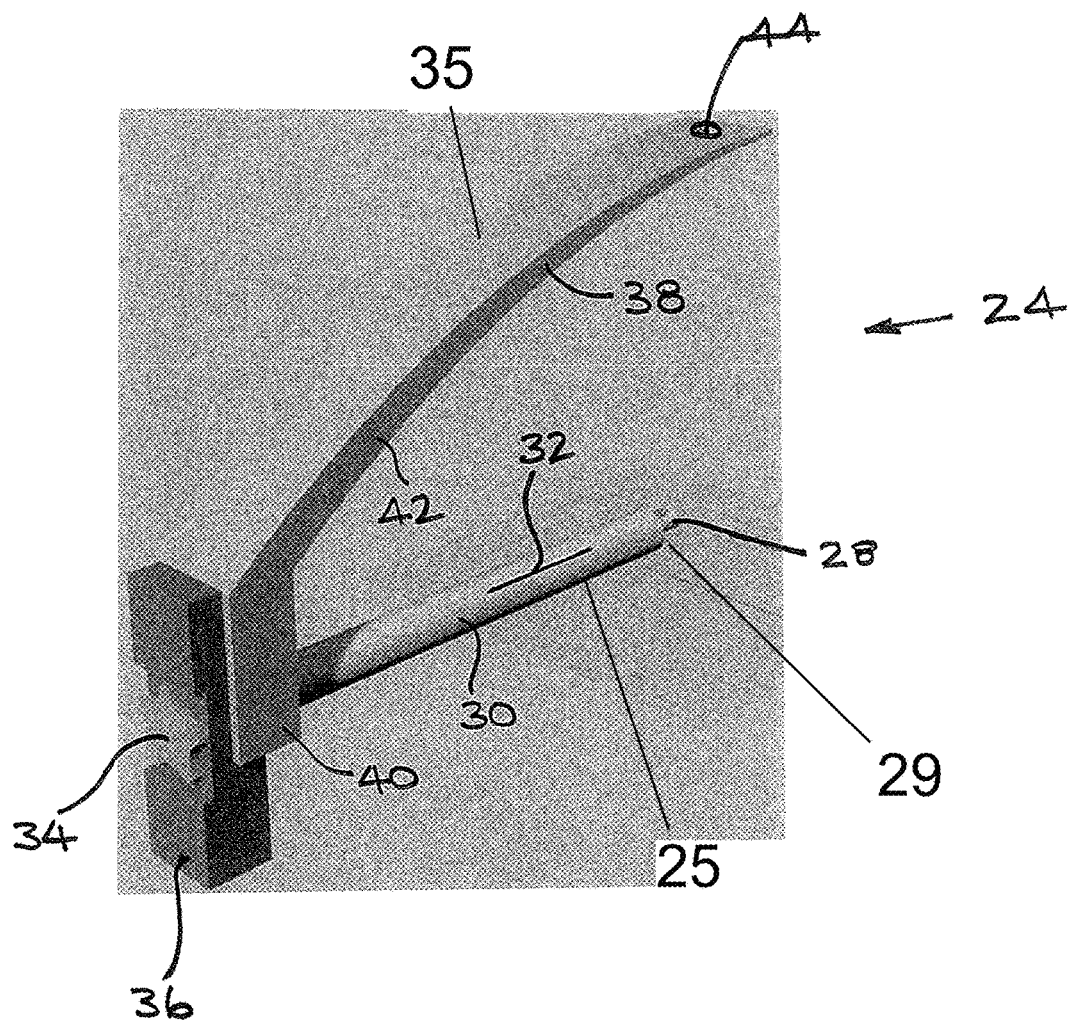
FIG. 3 is an isometric view showing portions of the device of FIG. 2.

FIGS. 2 and 3 show isometric views of an exemplary embodiment of a fixation device 24 according to the invention. As shown, the fixation device 24 includes a fixation arm 25 including a fixation screw 26 and aiming arm 35 including an aiming guide 38. In order to fix a fracture 15 using the device 24, first fastener, which is a fixation screw 26 in the embodiment shown, is inserted into the femur at a first angle using the fixation arm 25. Aiming guide 38 is then used to insert a second fastener, which is a set screw 52 in the embodiment shown, into the femur at a second angle, and into engagement with the fixation screw 26, stabilizing the fixation screw 26, as described in detail below. Although a femoral fracture is shown in and described, it should be understood that a device according to the invention could be applied to various types of bone fractures.

Still referring to FIGS. 2 and 3, the fixation arm 25 is shown in detail. As shown, the fixation arm 25 includes a shaft 28 having an elongate body with a first end 27 and a second end 29. The shaft 28 is housed within a tubular shroud 30 and includes a knob 34, extending from the second end 27 and configured for rotating the shaft 28. The fixation screw 26 is removably attached to the shaft 28, as described in detail below, and extends in an axial direction of the shaft 28 from the second end 29 thereof. The shaft 28 is positioned within the shroud 30 and is rotatable about its longitudinal axis 32 relative to the shroud 30 by manual rotation of the knob 34. The shaft 28 and knob 34 are housed within a handle 36, which as shown, is located near the first end 27 of the shaft 28, with the knob 34 protruding from an end thereof.

Still referring to FIGS. 2 and 3, the aiming arm 35 is removably mounted the shaft 28 at the first end 27 thereof. As shown, aiming arm 35 is mounted with the aiming guide 38 extending upward and in a curved path over the shaft 28, and in alignment with the shaft 28 in a direction from the first end 27 to the second end 29. The aiming guide 38 further includes a base 40 that attaches to the handle 36 and an arm 42 that extends from the base 40, the arm 42 having a first end 41 affixed to the base 40, and a second end 43 located opposite the first end 41.

A through hole 44 extends through the arm 42, near the second end 43 thereof. The curved path of the arm 42, extending over the fixation arm 25, allows the hole 44 to be positioned in alignment with a transverse opening 46 in the fixation screw 26 when the screw is mounted on shaft 28, as described in detail below. The hole 44 receives a guide sheath 48. As shown, the guide sheath 48 has an elongate body that extends from the second end 43 of the arm 42, towards the fixation arm 25, and in particular towards the fixation screw 26. Guide sheath 48 receives a Kirschner wire ("K-wire") guide 50 and, during a fracture treatment procedure, the K-wire guide is removed and the guide sheath 48 receives a set screw 52, as shown in FIG. 5 and described in further detail below.

Figure 4:
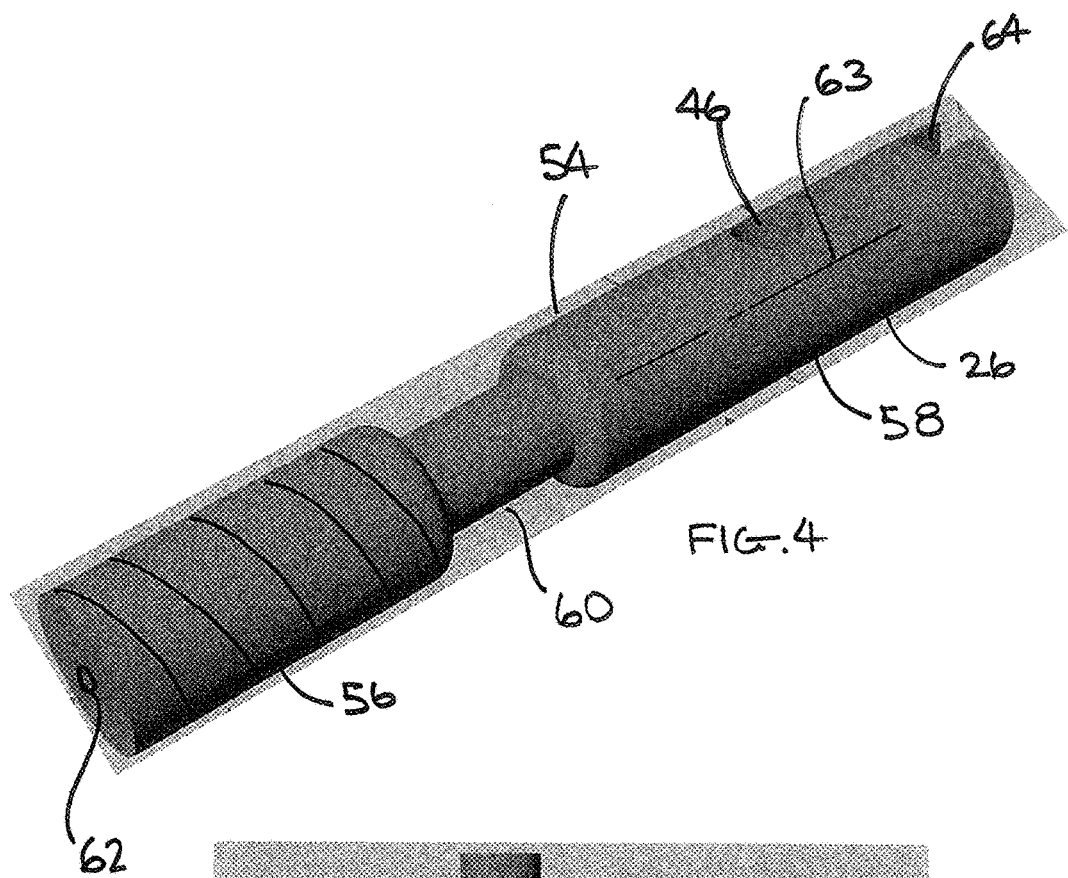
FIG. 4 is an isometric view of the fixation screw of the device of FIG. 2
Figure 5:
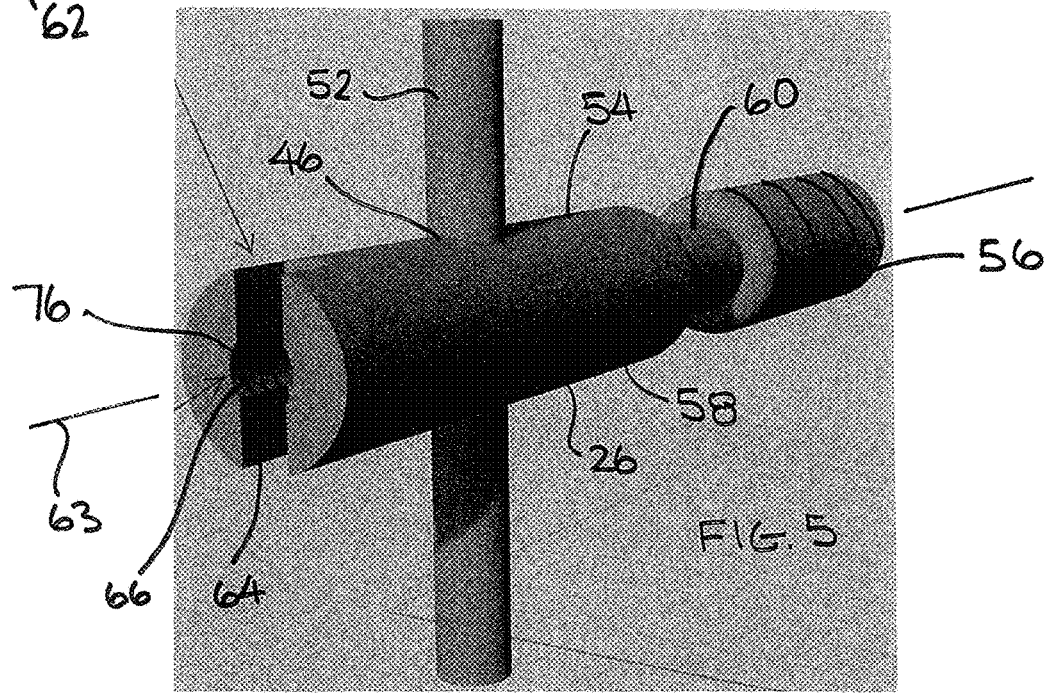
FIG. 5 is an isometric view of the fixation screw of FIG. 2, with a set screw housed therein.

FIGS. 4 and 5 show isometric views of the fixation screw 26 in detail. In the exemplary embodiment shown, the fixation screw 26 includes a rod 54 having a threaded end portion 56 which engages the femoral head 18 during a treatment procedure. Opposite the threaded end portion 56, rod 54 includes a smooth surfaced tang 58. Tang 58 and threaded end portion 56 are connected by a waist 60 having a smaller diameter than the tang 58 and the end portion 56. As shown, the fixation screw 26 is cannulated, with a cannula 62 extending along the longitudinal axis 32 and configured to allow for passage of a K-wire, as described below. Tang 58 is adapted to attach to shaft 28 and shroud 30. In the exemplary embodiment, as shown in FIG. 5, the tang 58 has a transverse slot 64, and a threaded bore 66, having internal threads 76, which is arranged coaxially with cannula 62, the threaded bore 66 extending along the slot 64. Other embodiments could employ other mechanisms for aligning and attaching the tang 58 to the shaft 28 and shroud 30. In one exemplary embodiment, the tang 58 could include multiple transverse slots, configured similarly to the slot 64 shown in FIG. 5, each of which engages with one of a plurality of fins, configured similarly to fin 72 shown in FIG. 6. In other embodiments, the slot 64 could be replaced with a recess having one of a variety of shapes, and the fin 72 could have a complimentary shape. Other engagement and alignment mechanisms known in the art could be employed as well.

Figure 11:
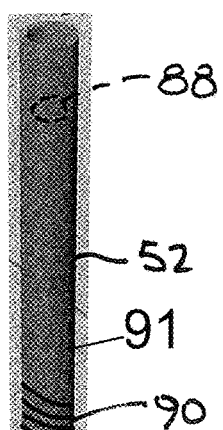
FIG. 11 is an isometric view of the set screw of the device of FIG. 2.

Tang 58 includes transverse opening 46 that receives the set screw 52 during the procedure treating the fracture, as described in detail below. The transverse opening 46 may include internal threads 90 for engagement with external threads formed on the set screw 52 (FIG. 11). In another embodiment, the transverse opening 46 could be provided free of threads, and rely on engagement of set screw threads 90 with the inner surface thereof to affix the set screw within the transverse opening 46.

In an embodiment, transverse opening 46 could be filled with or having the capability to receive a biodegradable polymer or biodegradable insert. In such an embodiment, the set screw 52 could pass through and engage the insert or biodegradable polymer, which could optionally include a cavity having inner threads for engagement with the exterior threads 90 of the set screw 52. Such an insert could be configured to fully degrade during the projected healing time of the fracture, facilitating disengagement and removal of the set screw 52 and fixation screw 26.

Figure 6:
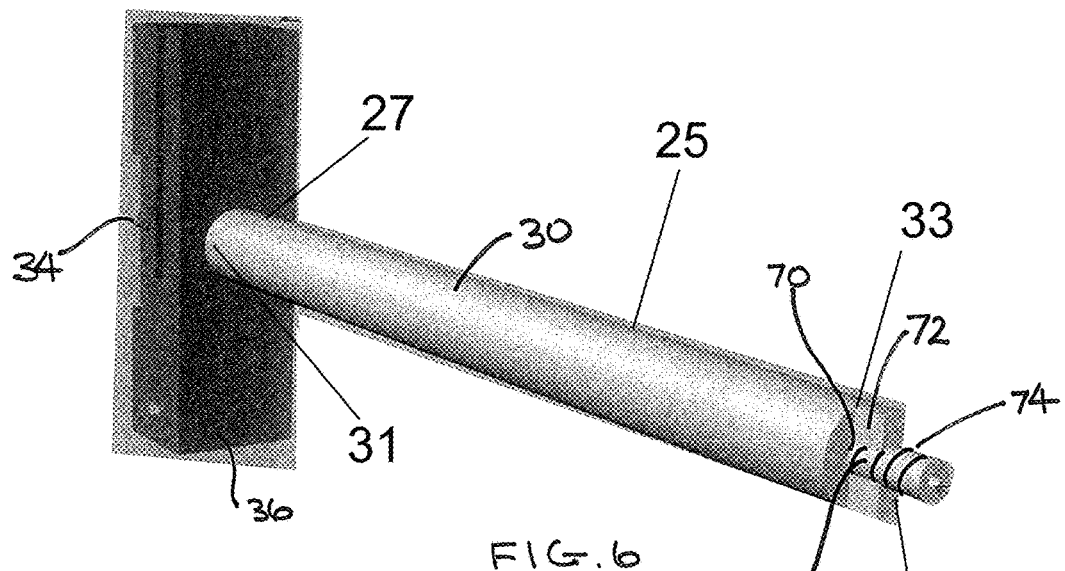
FIG. 6 is an isometric view of the shaft and shroud of the device of FIG. 2.
Figure 7:
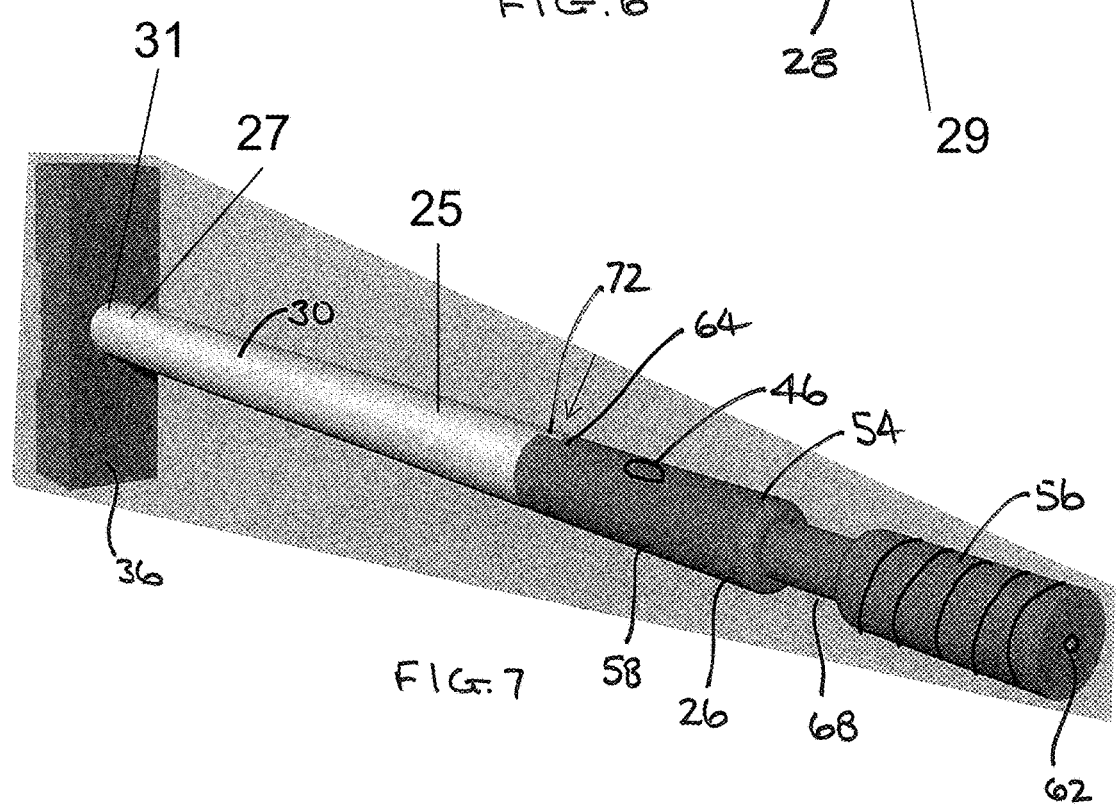
FIG. 7 is an isometric view of the shaft and shroud as shown in FIG. 6, with the fixation screw affixed thereto.

FIGS. 6 and 7 show isometric views of the shaft 28 and shroud 30. As shown, the shaft 28 is housed within a bore 70 defined in the shroud 30, extending along axis 32, and is rotatable relatively to the shroud 30 by turning the knob 34. A first end 31 of shroud 30 is fixedly attached to the handle 36, and a second end 33 has an axially projecting fin 72 that is adapted to engage the transverse slot 64 in the fixation screw 26, as shown in FIG. 7. Engagement of the fin 70 with slot 64 maintains a fixed alignment between the handle 36 and the transverse opening 46 in the fixation screw 26, thereby allowing the handle 36 to be an indicator of the orientation of the opening 46 during the procedure, as described below.

FIG. 7 shows the fixation screw 26 affixed to the shaft 28. The second end 29 of shaft 28 has external threads 74 that engage the internal threads 76 of the threaded bore 66 (see FIG. 5) of the fixation screw 26 when the fixation screw 26 is secured to the shaft 28 and shroud 30. The threaded engagement between the shaft 28 and the fixation screw 26 allows the fixation screw 26 to be removably attached to the shaft 28 and shroud 30, as required in order to execute the procedure for treatment of a fracture.

Figure 8:
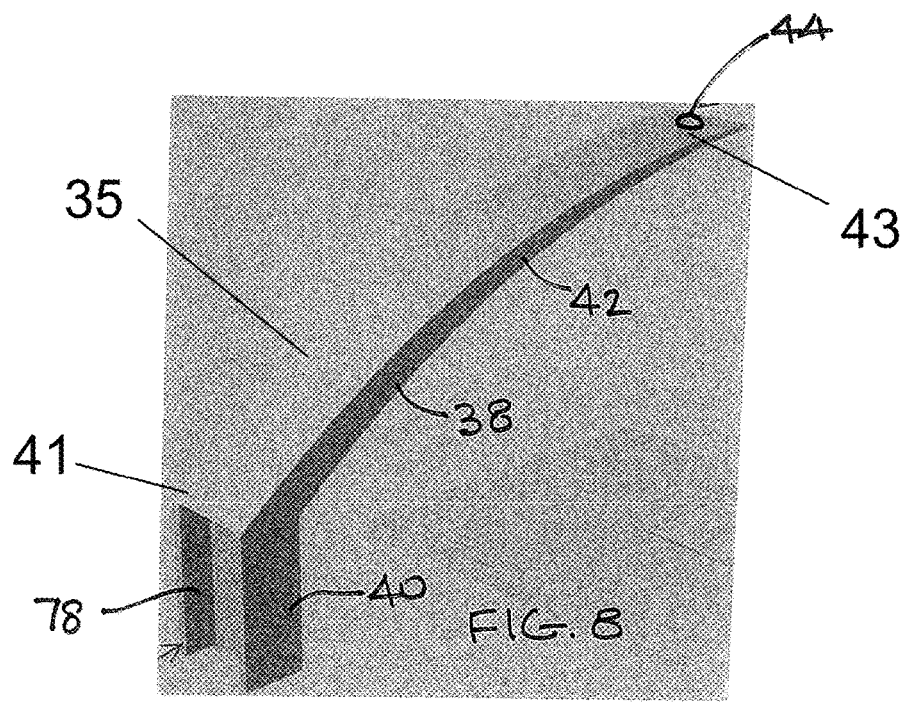
FIG. 8 is an isometric view showing portions of the aiming arm of the device of FIG. 2.

FIG. 8 shows an isometric view of the aiming guide 38 in detail. The base 40 of aiming guide 38 is adapted to receive handle 36, as shown in FIG. 3. In the embodiment shown, the base 40 includes a recess 78 having a complementary shape to that of the handle 36. In some embodiments, additional mating features, such as engageable grooves and rails may be positioned on the interfacing surfaces of the base 40 and handle 36 to provide secure engagement between the parts. In other embodiments, other mechanisms known in the art could be provided to affix the base 40 to the handle 36.

Figure 9:
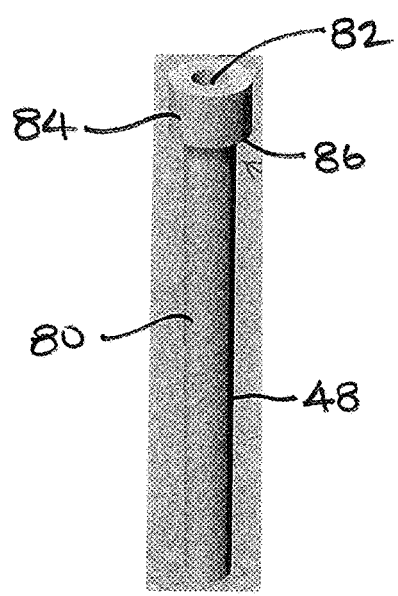
FIG. 9 is an isometric view of the guide sheath of the device of FIG. 2.
Figure 10:
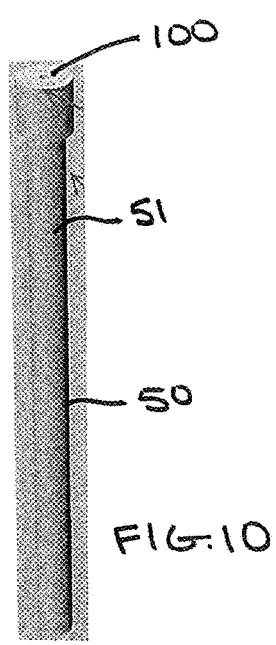
FIG. 10 is an isometric view of a K-wire guide of the device of FIG. 2.

As shown in FIG. 9, the guide sheath 48 includes a tube 80 defining a bore 82. A collar 84 is positioned at an upper end of the tube 80, the collar 84 having a larger diameter than the tube 80 and defining a shoulder 86. As shown in the exemplary embodiment of FIG. 2, when the guide sheath 48 is in position extending through the through hole 44, the shoulder 86 sits on an upper surface of the guide arm 42, fix the tube 80 in position on the arm 42. In other embodiments, the guide sheath 48 could be retained in place on the guide arm 42 using other mechanisms known in the art, such as releasable mechanical fasteners, for example, a threaded engagement between the guide sheath 42 and hole 44. Bore 82 is sized to receive two components, the K-wire guide 50, shown in detail in FIG. 10, and the set screw 52, shown in FIG. 11. Referring to FIG. 10, K-wire guide 50 includes a cannulated tube 51 that supports and guides a K-wire during a treatment procedure. Some embodiments may include engagement mechanisms to releasably affix the K-wire guide 50 in place within the bore 82 of guide sheath 48, such as complimentary threads formed on the K-wire guide 50 and bore 82, as well as other releasable mechanical fasteners known in the art.

The set screw 52 is also cannulated for controlled movement along the K-wire during the procedure. As shown in FIG. 11, the set screw 52 has a recessed head 88 at a top end, which is configured to receive a driver. Set screw 52 further includes an elongate shaft 91 having threads 90 at the bottom end thereof, the threads 90 being configured for engaging the femur during the procedure, as described below. In the embodiment shown in FIG. 11, the set screw head 88 is substantially flush with the shaft 91, but in other embodiments, the set screw 52 could have an enlarged head or proximal portion having a greater diameter than the shaft 91. In the embodiment shown, the threads 90 are formed in along a limited portion of the shaft 91 at the bottom end thereof, but in other embodiments, a larger portion of the shaft 91, or even the entire shaft 91 could be threaded. The threads 91 could be formed of various materials, for example being completely or partially formed of biocomposites, biodegradable polymers, metals, metal composites known to those skilled in the art. In examples where the threads are formed from biodegradable materials, such as biocomposites or other biodegradable materials, the threads could be configured to fully degrade during the projected healing time of the fracture, facilitating disengagement and removal of the set screw 52 from the fixation screw 26. In other embodiments, the second fastener 52 could take on configurations other than that of a set screw. For example, a non-threaded fastener such as a pin could be utilized and configured to engage the transverse opening 46 in a manner known in the art.

FIGS. 12-20 illustrate an exemplary procedure for treating a non-displaced femoral neck fracture using a device 24 according to the invention. The procedure may be executed under fluoroscopy.

Figure 12:
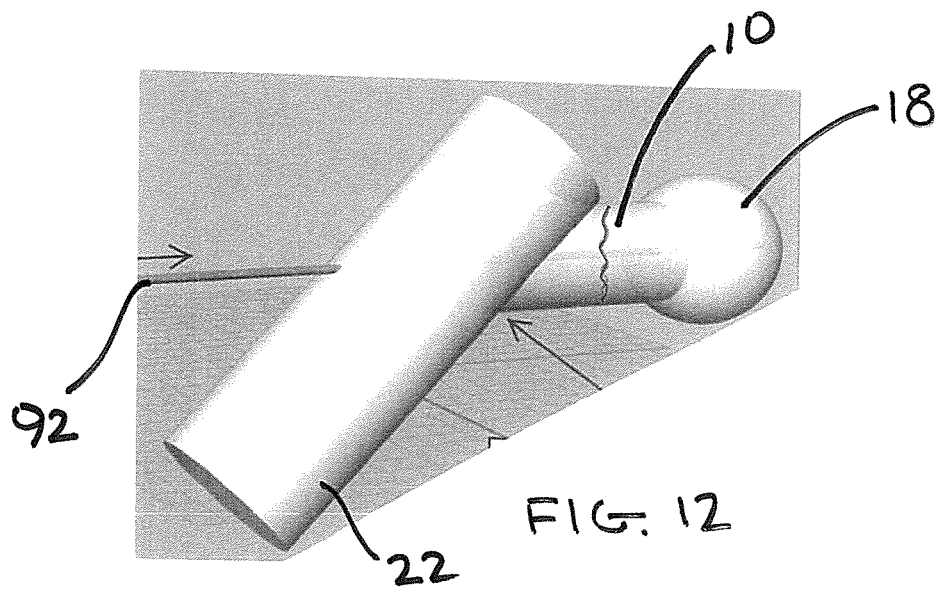
FIG. 12 is an isometric view showing a stage of a procedure for treating a femoral neck fracture using the device shown in FIG. 2.
Figure 13:
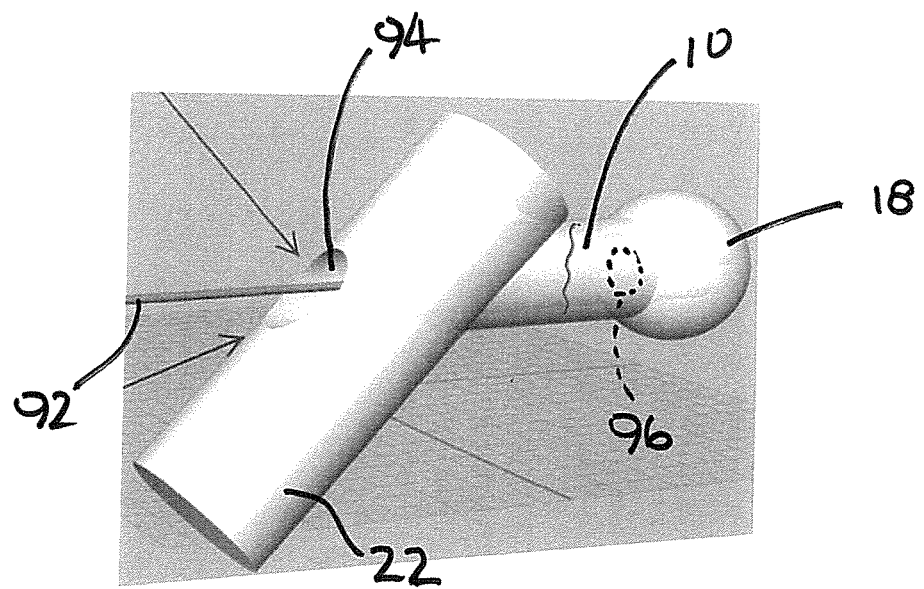
FIG. 13 is an isometric view showing another stage of a procedure for treating a femoral neck fracture using the device shown in FIG. 2.

Referring to FIG. 12, a first incision is made to provide an opening for over-drilling of the K-wire. As shown, a K-wire 92 is percutaneously driven through the femur 22, across the fracture site 15 into the femoral head 18 using a drill. As shown in FIG. 13, the femur 22, neck 10 and head 18 are over-drilled, which may be performed using a two diameter stepped drill bit, to form a clearance hole 94 in the femur 22 and neck 10. Clearance hole 94 extends in a first longitudinal direction, in axial alignment with the femur neck 10, and includes a portion that acts as a pilot hole 96 in the head 18.

Figure 14:
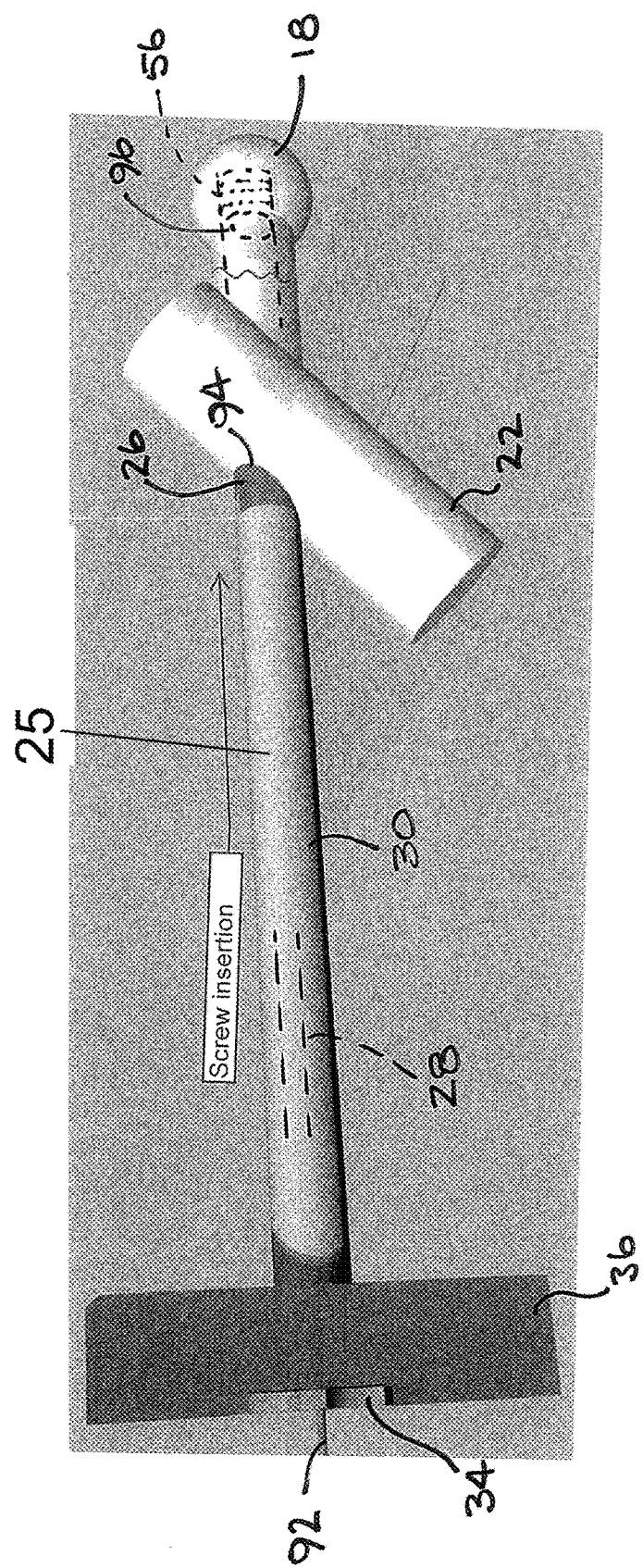
FIG. 14 is an isometric view showing another stage of a procedure for treating a femoral neck fracture using the device shown in FIG. 2.

As shown in FIG. 14, the fixation screw 26, which is attached to the shaft 28 and shroud 30, is then inserted over the K-wire, through the clearance hole 94 and into the pilot hole 96. As described above, the fixation screw 26 is fixed to the shroud 30 by way of the engagement between the fin 72 of shroud 30 and slot 64 in the fixation screw 26 (see FIG. 7), and is retained in position on the shroud 30 by threaded engagement with the shaft 28. Rotation of the handle 34 rotates the entire fixation arm 25, and due to the coupling between the shroud 30 and fixation screw 26, in turn rotates the fixation screw 26, causing threads on the threaded end portion 56 to bite into the femur head 18 within the pilot hole 96 and secure the fixation screw 26 to the femur head.

Figure 15:
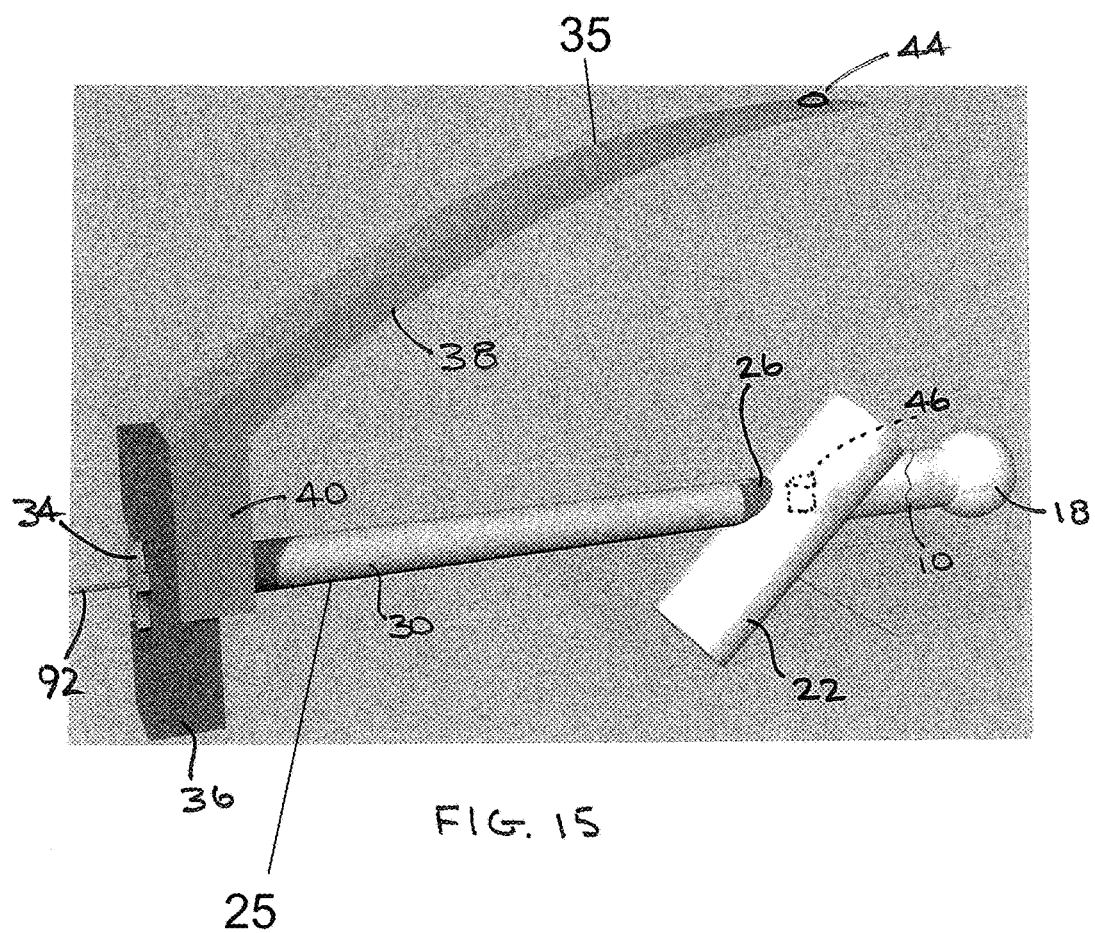
FIG. 15 is an isometric view showing another stage of a procedure for treating a femoral neck fracture using the device shown in FIG. 2.
Figure 16:
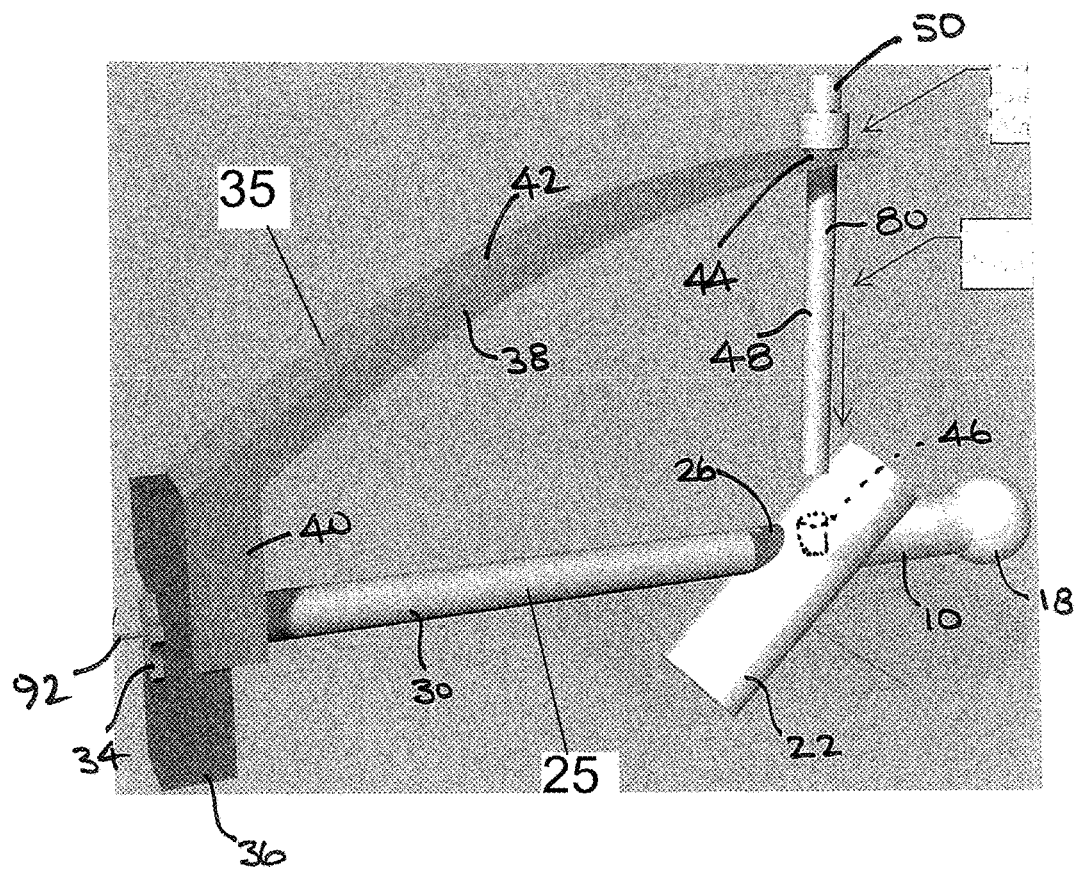
FIG. 16 is an isometric view showing another stage of a procedure for treating a femoral neck fracture using the device shown in FIG. 2.
Figure 17:
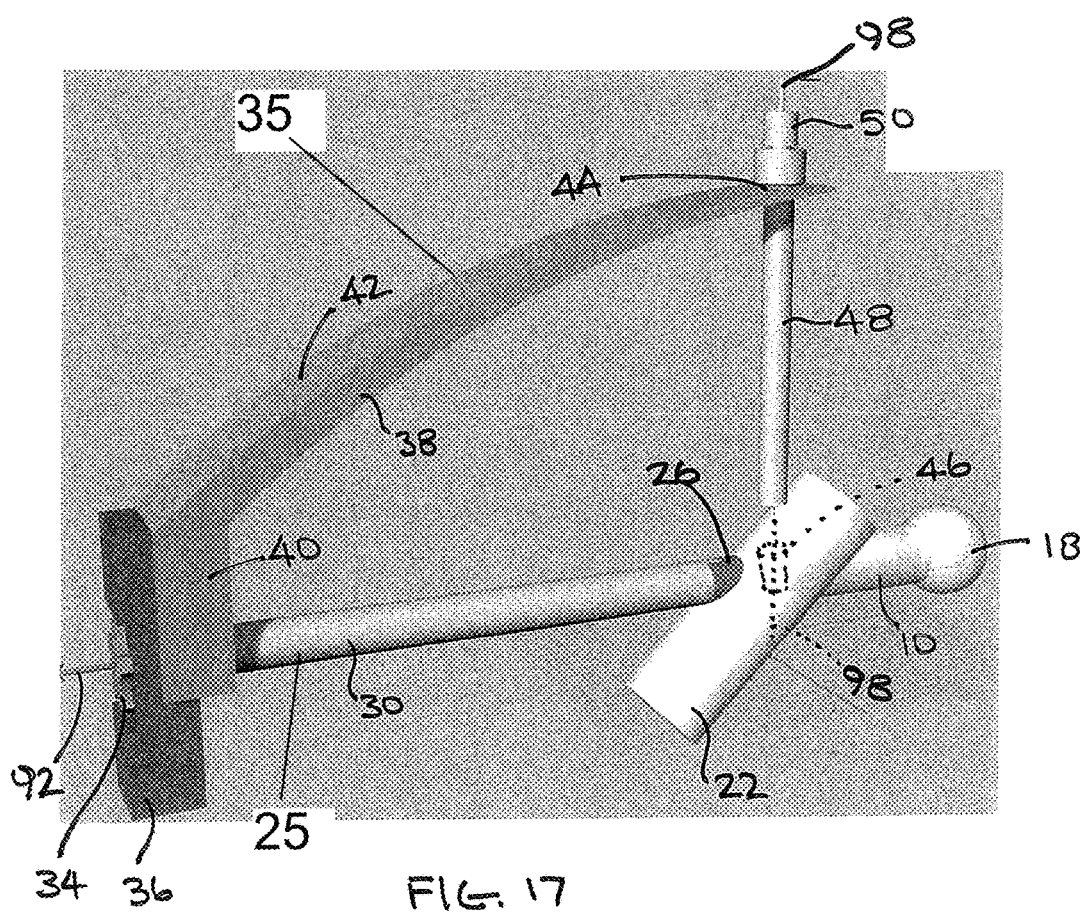
FIG. 17 is an isometric view showing another stage of a procedure for treating a femoral neck fracture using the device shown in FIG. 2.
Figure 18:
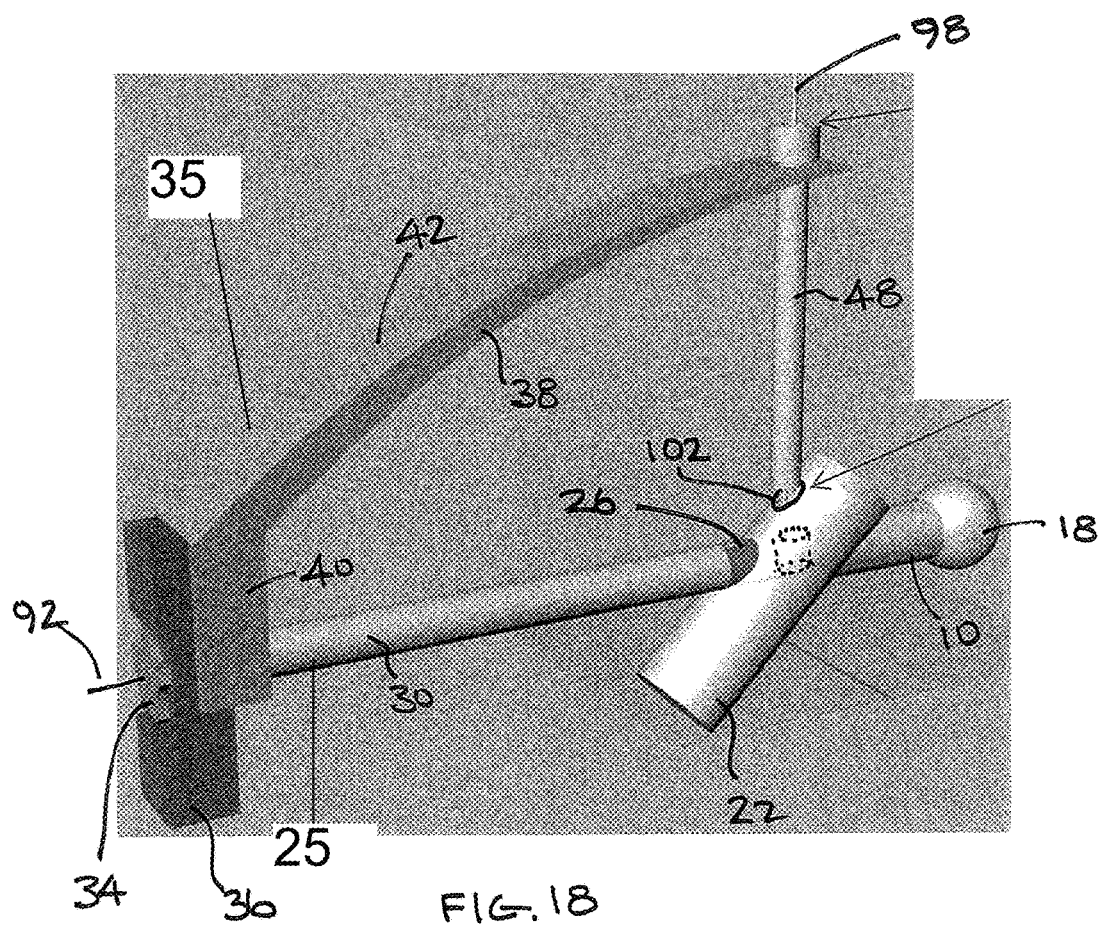
FIG. 18 is an isometric view showing another stage of a procedure for treating a femoral neck fracture using the device shown in FIG. 2.

As shown in FIG. 15, the aiming arm 35 is affixed to the fixation arm 25, with the aiming guide 38 mounted onto the handle 36, the handle 36 being received within the recess 78 of the base 40. The handle 36 aligns lengthwise with the fin 72 of shroud 30, and the transverse opening 46 in the fixation screw 26 also aligns radially with the fin 72 (see FIG. 7). Furthermore, the hole 44 in arm 42 aligns with the transverse opening 46, whose angular position is known by the position of handle 36. Handle 36 is adjusted so that the transverse opening 46 is coaxially aligned with hole 44. A second incision is made to admit the guide sheath 48 to the fracture site, as shown in FIGS. 16 and 17. As shown in FIG. 16, the guide sheath 48 passes through hole 44 in arm 42 and aligns with the transverse opening 46 in the fixation screw 26. The K-wire guide 50 is housed within the bore 82 of tube 80 of the guide sheath 48, and second K-wire 98 is housed within the cannula 100 of K-wire guide 50. As shown in FIG. 17, the second K-wire 98 is inserted through the cannula 100 of the K-wire guide 50 (see FIG. 10) and forced through the femur 22 and through the transverse opening 46 of the fixation screw 26. As shown in FIG. 18, the K-wire guide 50 is then removed and the K-wire 98 is overdrilled to form a set screw hole 102 in femur 22. The set screw hole 102 extends in a second longitudinal direction, which intersects the first longitudinal direction. In some embodiments, the first and second longitudinal directions may be substantially perpendicular, and in other embodiments they may be oriented at non-right angles with respect to each other, depending on the patient's anatomy and the location and configuration of the fracture.

Figure 19:
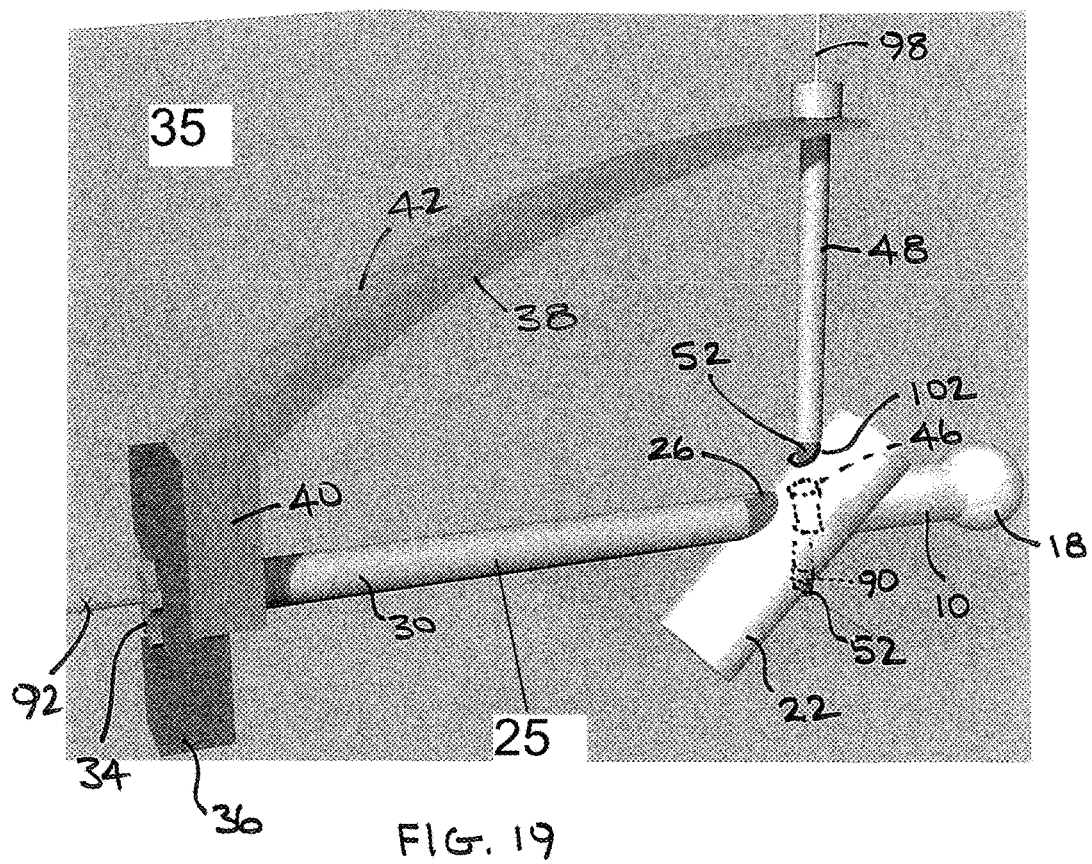
FIG. 19 is an isometric view showing another stage of a procedure for treating a femoral neck fracture using the device shown in FIG. 2.

FIG. 19 shows the set screw 52 passed along K-wire 98, through the hole 102 in femur 22 and through the transverse opening 46 in the fixation screw 26. The set screw 52 is then rotated via a cannulated long bit driver (not shown) that engages the set screw by its head 88 (see FIG. 11), and the threads 90 of the set screw 26 engage and advance through the femur, below the fixation screw 26 to secure the set screw 52 in place.

Figure 20:
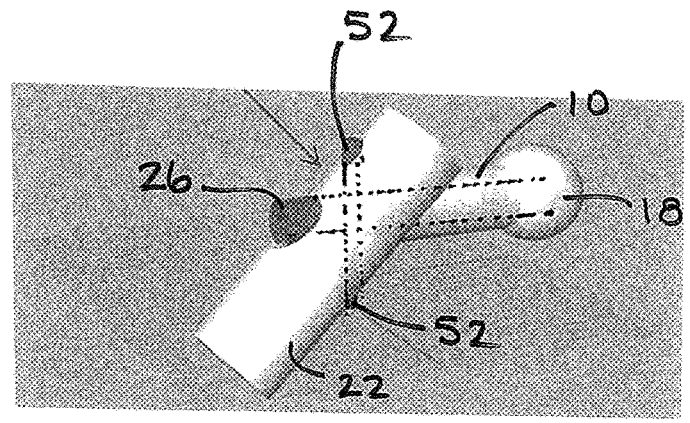
FIG. 20 is an isometric view showing another stage of a procedure for treating a femoral neck fracture using the device shown in FIG. 2.

FIG. 20 shows the femur 22 at the end of the procedure. The driver and K-wire 98 are removed, the aiming guide is removed from handle 36 and the sheath 30 and shaft 28 are disengaged from the fixation screw 28 by rotating the knob 34 to unscrew shaft 28 from the internal threads 76 of the threaded bore 66 in the tang 58 of the fixation screw 26, thereby allowing the shaft 28 and shroud 30 to be withdrawn. The incisions are then closed, completing the procedure.

Figure 21:
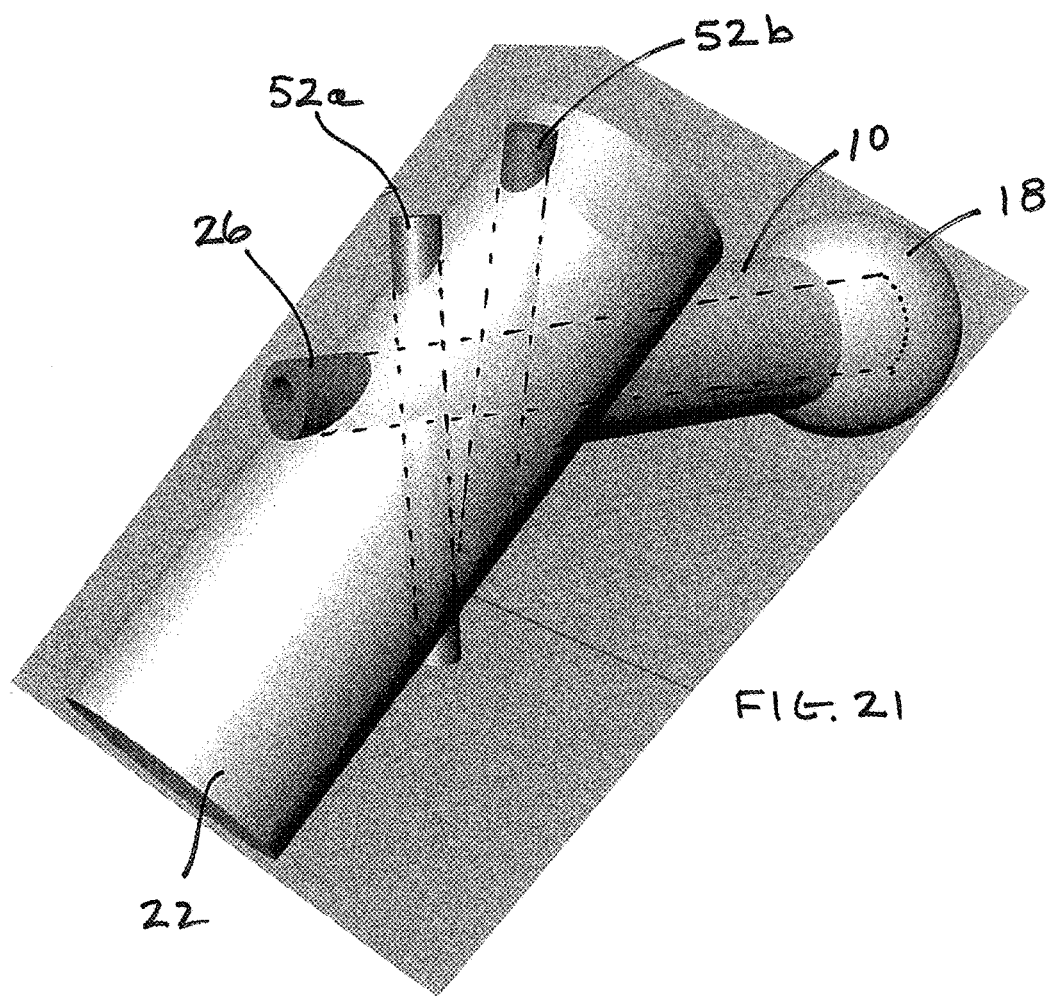
FIG. 21 is a side isometric view of another embodiment of a device for treatment of a femoral neck fracture.
Figure 22:
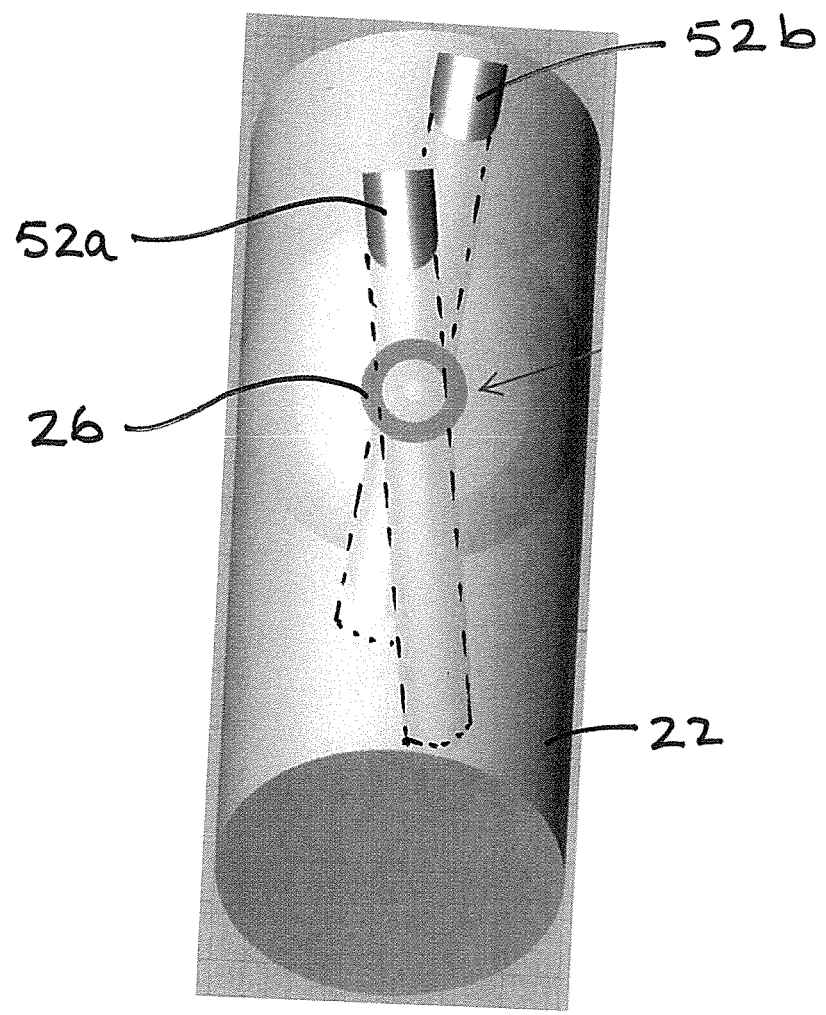
FIG. 22 is a top isometric view of the device of FIG. 21.

Another embodiment of a device 24 according to the invention is shown in FIGS. 21 and 22. This embodiment of the device 24 is similar to that shown in FIGS. 1-20 and described above, but includes two set screws 52a and 52b in place of the single set screw 52 described above. The use of two set screws may increase stability and prevent rotation about the fixation screw axis, as well as fracture collapse. The two set screws 52a, 52b are in spaced relation to one another along the fixation screw 26 and may be angularly oriented relative to one another, as shown in FIG. 22. The spacing and angular orientation of the two set screws 52a, 52b may be varied, depending on the anatomy of the patient, as well as the location and dimensions of the fracture. The aiming arm 42 of this embodiment would be provided with two thorough holes 44, each accommodating an associated guide sheath 48 and K-wire guide 50, and such modifications would be within the purview of one skilled in the art.

Yet another embodiment of a device 24 according to the invention is shown in FIG. 23. This embodiment of the device 24 is similar to that shown in FIGS. 1-20 and descried above, but is adapted to treat displaced fractures. As shown in FIG. 23, to treat a displaced fracture, a compression barrel 104 is threadedly engaged with the shroud 30, which, in this exemplary embodiment, includes external threads 106 that engage internal threads on the inner surface of the compression barrel (not shown). The compression barrel 104 may include knob 108, and rotation of the knob 108 may be used to rotate the compression barrel 104 about the shroud 30. Due to the threaded engagement between the compression barrel 104 and shroud 30, rotation of the compression barrel 104 moves the compression barrel 104 in an axial direction along the length of the shroud 30, towards the femur 22. When the barrel 104 engages the femur 22, further rotation draws the shroud 30, along with the shaft 28 and the fixation screw 26 away from the femur 22, thereby drawing the femur head 18 toward the femur 22 and into engagement with the femur neck 10 to join the previously displaced fracture. In another embodiment, the internal threads could be omitted from the compression barrel 104 and provided instead on an inner surface of the knob 108, with the compression barrel 104 slidably receiving the shroud, such that rotation of the knob 108 and engagement of the inner threads of the knob 104 with the outer threads 106 of the shroud 30 moves the compression barrel 104 towards the femur, as described above.

While the preferred embodiments of the invention have been described in detail above, the invention is not limited to the specific embodiments described, which should be considered as merely exemplary.

What is claimed is:

1. A bone fixation device for treatment of a bone fracture, comprising:
   a first fastener including a threaded end portion and defining a transverse opening;
   a fixation arm configured for inserting the first fastener through a bone fracture and engaging a femoral head via the threaded end portion;
   a second fastener; and
   aiming arm configured for inserting the second fastener into the transverse opening and engagement with the first fastener;
   wherein the first fastener stabilizes the second fastener in a non-threaded engagement and the second fastener is configured with threading to engage the bone;
   wherein the first fastener is configured to engage only interior surfaces of the bone having the bone fracture.

2. The fixation device of claim 1, wherein the fixation arm is configured for inserting the first fastener at a first angle, and the aiming arm is configured for inserting the second fastener at a second angle, substantially perpendicular to the first angle.

3. The fixation device of claim 1, wherein:
   the fixation arm comprises a rotatable shaft;
   the first fastener is a fixation screw, and is rotationally affixed to an end of the shaft, such that rotation of the shaft rotates the fixation screw.

4. The fixation device of claim 1, wherein the first fastener defines an axially extending cannula configured to receive a Kirschner wire.

5. The fixation device of claim 1, wherein the fixation arm comprises a rotatable shaft, wherein the aiming arm is affixed to a first end of the shaft, and the first fastener is attached to a second end of the shaft.

6. The fixation device of claim 5, wherein the aiming arm comprises a first end affixed to the fixation arm, and a second end positioned for aligning the second fastener with the transverse opening.

7. The fixation device of claim 6, wherein the aiming arm comprises an elongate aiming guide that extends over the fixation arm and is configured for aligning the second fastener with the transverse opening.

8. The fixation device of claim 7, further comprising a guide sheath that extends through the through hole, the guide sheath having an elongate body that extends towards the first fastener, for positioning the second fastener within the transverse opening.

9. The fixation device of claim 1, wherein the fixation arm comprises a rotatable shaft, wherein the fixation arm further comprises a shroud having a substantially tubular body that houses the shaft, the shaft being configured to rotate within the shroud.

10. The fixation device of claim 1, wherein the first fastener has a longitudinal cannula therethrough, the cannula being open through the first fastener at longitudinal ends of the fastener and at the transverse opening.

11. A bone fixation device for treatment of a femoral neck fracture, located between the femur and femur head regions, the device comprising:
   a fixation screw having a threaded end portion and defining a transverse opening;
   a fixation arm configured for inserting the fixation screw through the femur at a first angle to engage a femoral head via the threaded end portion, the fixation arm having an elongate body including a first end and a second end, and the fixation screw releasably affixed at the second end of the body;

a set screw; and an aiming arm configured for inserting the set screw through the femur at a second angle, into the transverse opening and engagement with the fixation screw, the aiming arm being affixed to the first end of the fixation arm and extending over the fixation arm to position the set screw in alignment with the transverse opening;

wherein the set screw stabilizes the fixation screw in a non-threaded engagement and the set screw is configured with threading to engage the femur;

wherein the fixation screw is configured to engage only interior surfaces of the femur.

12. The bone fixation device of claim 11, wherein: the fixation screw is rotationally affixed to the fixation arm, such that rotation of the fixation arm rotates the fixation screw.

13. The bone fixation device of claim 11, wherein the aiming arm comprises an elongate aiming guide that extends over the fixation arm and comprises at least one through hole aligned with the transverse opening.

14. The bone fixation device of claim 13, further comprising a guide sheath that extends through the through hole, the guide sheath having an elongate body that extends towards the fixation screw, for positioning the set screw within the transverse opening.

15. The bone fixation device of claim 11, wherein the fixation arm comprises a rotatable shaft, wherein the fixation arm further comprises a shroud having a substantially tubular body that houses the shaft, the shaft being configured to rotate within the shroud.

16. The bone fixation device of claim 11, wherein the first fastener has a longitudinal cannula therethrough, the cannula being open through the first fastener at longitudinal ends of the fastener and at the transverse opening.

17. A method of fixing a bone fracture, comprising: providing a bone fixation device, the device comprising:

a fixation screw having a threaded end portion and defining a transverse opening;

a fixation arm configured for inserting the fixation screw through the femur at a first angle to engage a femoral head via the threaded end portion, the fixation arm having an elongate body including a first end and a second end and the fixation screw releasably affixed at a the second end of the body;

a set screw; and an aiming arm configured for inserting the set screw through the femur at a second angle substantially perpendicular to the first angle, into the transverse opening and engagement with the fixation screw, the aiming arm being affixed to the first end of the fixation arm and extending over the fixation arm to position the set screw in alignment with the transverse opening;

drilling a first opening through the bone fracture to create a passage to a pilot hole, the first opening extending in a first longitudinal direction;

using the fixation arm to insert the fixation screw into the pilot hole;

drilling a second opening extending in a second direction that intersects the first longitudinal direction;

using the aiming arm to insert the set screw into the transverse opening, to stabilize the fixation screw in a non-threaded engagement and the set screw fastener is configured with threading to engage the femur;

wherein the fixation screw engages only interior surfaces of the femur.

18. The method of claim 17, wherein the fixation screw is rotationally fixed with respect to the fixation arm, the method comprising rotating the fixation arm to engage the fixation screw within the pilot hole.

19. The method of claim 17, wherein the device further comprises a guide sheath affixed to the aiming arm, the method further comprising inserting the guide sheath into the transverse opening to guide the set screw into the transverse opening.

20. The method of claim 17, wherein the first fastener has a longitudinal cannula therethrough, the cannula being open through the first fastener at longitudinal ends of the fastener and at the transverse opening.

* * * * *